US012702134B2

(12) United States Patent
Cassayre et al.

(10) Patent No.: US 12,702,134 B2
(45) Date of Patent: Aug. 11, 2026

(54) AGROCHEMICAL COMPOUNDS

(71) Applicant: SYNGENTA CROP PROTECTION LLC, Greensboro, NC (US)

(72) Inventors: Jérôme Yves Cassayre, Stein (CH); Peter Renold, Stein (CH); Myriem El Qacemi, Stein (CH); Thomas Pitterna, Stein (CH); Julie Clementine Toueg, Stein (CH)

(73) Assignee: SYNGENTA CROP PROTECTION LLC, Greensboro, NC (US)

(*) Notice: Subject to any disclaimer, the term of this patent is extended or adjusted under 35 U.S.C. 154(b) by 912 days.

(21) Appl. No.: 17/839,058

(22) Filed: Jun. 13, 2022

(65) Prior Publication Data

US 2023/0000082 A1 Jan. 5, 2023

Related U.S. Application Data

(60) Continuation-in-part of application No. 17/000,978, filed on Aug. 24, 2020, now Pat. No. 11,357,231, which is a division of application No. 16/267,562, filed on Feb. 5, 2019, now Pat. No. 10,750,745, which is a division of application No. 15/429,631, filed on Feb. 10, 2017, now Pat. No. 10,206,400, which is a continuation of application No. 14/258,079, filed on Apr. 22, 2014, now Pat. No. 9,609,869, which is a continuation of application No. 13/512,820, filed as application No. PCT/EP2010/068605 on Dec. 1, 2010, now Pat. No. 8,735,362.

(30) Foreign Application Priority Data

Dec. 1, 2009 (EP) .................................... 09177640
Oct. 5, 2010 (EP) .................................... 10186537

(51) Int. Cl.

| | |
|---|---|
| ***A01N 43/80*** | (2006.01) |
| ***C07D 261/04*** | (2006.01) |
| ***C07D 413/12*** | (2006.01) |
| ***C07D 413/14*** | (2006.01) |
| ***C07D 417/12*** | (2006.01) |
| ***C07D 419/12*** | (2006.01) |

(52) U.S. Cl.
CPC ........... *A01N 43/80* (2013.01); *C07D 261/04* (2013.01); *C07D 413/12* (2013.01); *C07D 413/14* (2013.01); *C07D 417/12* (2013.01); *C07D 419/12* (2013.01)

(58) Field of Classification Search
CPC ..... A01N 43/80; C07D 261/04; C07D 413/12
See application file for complete search history.

(56) References Cited

U.S. PATENT DOCUMENTS

| | | | |
|---|---|---|---|
| 2,840,565 | A | 6/1958 | Holley et al. |
| 2,845,432 | A | 7/1958 | Keuhi, Jr. et al. |
| 2,929,836 | A | 3/1960 | Carrara |
| 4,639,771 | A | 1/1987 | Hattori et al. |
| 5,015,630 | A | 5/1991 | Fisher et al. |
| 5,478,855 | A | 12/1995 | Suzuki et al. |
| 2007/0066617 | A1 | 3/2007 | Mita et al. |
| 2009/0156643 | A1 | 6/2009 | Visser |

FOREIGN PATENT DOCUMENTS

| | | | |
|---|---|---|---|
| DE | 19520936 | A1 | 12/1996 |
| EP | 0367460 | A2 | 3/1990 |
| EP | 0382173 | A2 | 8/1990 |
| EP | 0444964 | A1 | 9/1991 |
| EP | 0503538 | A1 | 9/1992 |
| EP | 0535645 | A2 | 9/1992 |
| EP | 0535645 | A3 | 9/1992 |
| EP | 0594291 | A1 | 4/1994 |
| EP | 1731512 | A1 | 12/2006 |
| EP | 1932836 | A1 | 6/2008 |
| EP | 1997813 | | 12/2008 |
| EP | 2151437 | | 2/2010 |
| EP | 2186804 | | 5/2010 |
| EP | 2199287 | | 6/2010 |
| EP | 2412239 | | 7/2011 |
| EP | 2412240 | | 7/2011 |
| EP | 2412241 | | 7/2011 |
| EP | 2412238 | | 2/2012 |

(Continued)

OTHER PUBLICATIONS

U.S. Appl. No. 17/000,978, filed Aug. 24, 2020.

(Continued)

*Primary Examiner* — Kamal A Saeed
(74) *Attorney, Agent, or Firm* — BakerHostetler; Toni-Junell Herbert

(57) ABSTRACT

The disclosure is related to a compound of Formula (I), and compositions and methods of use thereof.

14 Claims, 2 Drawing Sheets

(56) References Cited

FOREIGN PATENT DOCUMENTS

| | | | |
|---|---|---|---|
| EP | 0626375 | A1 | 1/2026 |
| JP | 2007/008914 | A | 1/2007 |
| JP | 2007/016017 | | 1/2007 |
| JP | 2007/91708 | | 4/2007 |
| JP | 2007/106756 | | 4/2007 |
| JP | 2008/110971 | | 5/2008 |
| JP | 2008/133273 | | 6/2008 |
| JP | 2008/239511 | | 10/2008 |
| JP | 2009/108048 | | 5/2009 |
| JP | 2010/83883 | | 4/2010 |
| JP | 2010/235590 | | 10/2010 |
| JP | 2010/254529 | | 11/2010 |
| JP | 2011/178673 | | 9/2011 |
| JP | 2012/31093 | | 2/2012 |
| JP | 2012/31094 | | 2/2012 |
| JP | 2012/31095 | | 2/2012 |
| JP | 2012/31148 | | 2/2012 |
| JP | 2012/51843 | | 3/2012 |
| TW | 2008/04315 | | 1/2008 |
| TW | 2008/04315 | A | 1/2008 |
| TW | 2009/26983 | A | 7/2009 |
| TW | I355898 | B | 1/2012 |
| WO | 93/19053 | A1 | 9/1993 |
| WO | 93/25543 | A2 | 12/1993 |
| WO | 94/15944 | A1 | 7/1994 |
| WO | 94/19334 | A1 | 9/1994 |
| WO | 95/19363 | A1 | 7/1995 |
| WO | 95/22552 | A1 | 8/1995 |
| WO | 96/11945 | A2 | 4/1996 |
| WO | 96/15121 | A1 | 5/1996 |
| WO | 03/024222 | A1 | 3/2003 |
| WO | 2004/072086 | A2 | 8/2004 |
| WO | 05085216 | A1 | 9/2005 |
| WO | 2007/002696 | A2 | 1/2007 |
| WO | 07026965 | A1 | 3/2007 |
| WO | 2007/070606 | | 6/2007 |
| WO | 2007/074789 | A1 | 7/2007 |
| WO | 2007/075459 | | 7/2007 |
| WO | 2007/079162 | A1 | 7/2007 |
| WO | 2007/123853 | | 11/2007 |
| WO | 2007/123865 | | 11/2007 |
| WO | 2007/125984 | | 11/2007 |
| WO | 2008/016811 | A2 | 2/2008 |
| WO | 2008/019760 | | 2/2008 |
| WO | 2008/033562 | A2 | 3/2008 |
| WO | 2008/126565 | | 3/2008 |
| WO | 2008/053942 | A1 | 5/2008 |
| WO | 2008/122375 | | 10/2008 |
| WO | 2008/128711 | | 10/2008 |
| WO | 2008/130651 | | 10/2008 |
| WO | 2008/003075 | | 12/2008 |
| WO | 2008/150393 | | 12/2008 |
| WO | 2008/153942 | A1 | 12/2008 |
| WO | 2008/154528 | | 12/2008 |
| WO | 2009/002809 | | 12/2008 |
| WO | 09001942 | A1 | 12/2008 |
| WO | 2009/024541 | | 2/2009 |
| WO | 2009/049846 | | 4/2009 |
| WO | 2009/051956 | | 4/2009 |
| WO | 2009045999 | | 4/2009 |
| WO | 2009/072621 | | 6/2009 |
| WO | 2009/077197 | | 6/2009 |
| WO | 2009/080250 | A2 | 7/2009 |
| WO | 09080250 | A2 | 7/2009 |
| WO | 2009/097992 | | 8/2009 |
| WO | 2009/112275 | | 9/2009 |
| WO | 2009/141096 | | 11/2009 |
| WO | 2010/003877 | | 1/2010 |
| WO | 2010/003923 | | 1/2010 |
| WO | 2010/020521 | | 2/2010 |
| WO | 2010/020522 | | 2/2010 |
| WO | 2010/025998 | | 3/2010 |
| WO | 2010/032437 | | 3/2010 |
| WO | 2010/043319 | | 4/2010 |
| WO | 2010/070068 | | 6/2010 |
| WO | 2010/072602 | | 7/2010 |
| WO | 2010/072781 | | 7/2010 |
| WO | 2010/079077 | | 7/2010 |
| WO | 2010/084067 | | 7/2010 |
| WO | 2010/086225 | A1 | 8/2010 |
| WO | 2010/108733 | | 9/2010 |
| WO | 2010/112545 | | 10/2010 |
| WO | 2010/124845 | | 11/2010 |
| WO | 2010/133336 | | 11/2010 |
| WO | 2010/149506 | | 12/2010 |
| WO | 2011/37817 | | 2/2011 |
| WO | 2011/051455 | | 5/2011 |
| WO | 2011/054871 | | 5/2011 |
| WO | 2011/073444 | | 6/2011 |
| WO | 2011/075591 | | 6/2011 |
| WO | 2011/092287 | | 8/2011 |
| WO | 2011/101229 | | 8/2011 |
| WO | 2011/101402 | | 8/2011 |
| WO | 2011/104087 | | 9/2011 |
| WO | 2011/104088 | | 9/2011 |
| WO | 2011/104089 | | 9/2011 |
| WO | 2011/124998 | | 10/2011 |
| WO | 2011/128299 | | 10/2011 |
| WO | 2011/149749 | | 12/2011 |
| WO | 2011/154433 | | 12/2011 |
| WO | 2011/154434 | | 12/2011 |
| WO | 2011/154494 | | 12/2011 |
| WO | 2011/157748 | | 12/2011 |
| WO | 2011/167733 | | 12/2011 |
| WO | 2012/004326 | | 1/2012 |
| WO | 2012/007426 | | 1/2012 |
| WO | 2012/017359 | | 2/2012 |
| WO | 2012/026403 | | 3/2012 |
| WO | 2012/034957 | | 3/2012 |
| WO | 2012/035011 | | 3/2012 |
| WO | 2012/038851 | | 3/2012 |
| WO | 2012/045700 | | 4/2012 |
| WO | 2012/049327 | | 4/2012 |
| WO | 2012/060317 | | 5/2012 |
| WO | 2012/067235 | | 5/2012 |

OTHER PUBLICATIONS

Ozoe et al.: "The antiparasitic isoxazoline A1443 is a potent blocker of insect ligand-gated chloride channels" in: Biochemical and Biophysical Research Communications, 391, 2010, 744-749.

De Amici, Marco et al; "Chemoenzymatic Synthesis of Acetyl (R)-(+)- and (S)-(−)-Cycloserine" in: TetrIIMdron: Asymmetry vol. 4, No. 5, pp. 1073-1080, 1993.

Plattner, PI. A. et al.: "Synthesen des 4-Amino-3-isoxazolidinons (Cycloserin) und einiger Analoga" in: Helvetica Chimica Acta XL/v (1957), pp. 1531-52.

Kinney, William A. &al.: "Design and Synthesis of[2-(8,9-Dioxo-2,6-diazabicyclo[5 2.0]non-1(7)-en-2-yl)-ethyl|phosphonic Acid (EAA-090), a Potent N-Methyl-D-aspartate Antagonist, via the Use of 3-Cyclobutene-1,2-dione as an Achiral r-Amino Acid Bioisostere" in: J. Med. Chem, 1998, 41, 235-246.

Liskamp, Rob M.J. &al: "Synthesis and Ring-Opening Reactions of Functionalized Sullines. A New Approach to Sparsomycin" in: J. Org. Chem. 1981,46, 5408-5413.

De Amici, Marco &al: "Nitrile Oxides in Medicinal Chemistry—2:. Synthesis of the Two Enantiomers of Dihydromuscimol" in: Tetrahedron, vol. 45, No. 5, pp. 1975-1986.1990.

Nouvet, André et al: "Synthesis of perhydrodiazepinones as new putative peptidomimetics" in: Tetrahedron 55 (1999) 4685-4698.

Tse, Bruno: "Total Synthesis of (−)-Galbonolide B and the Determination of Its Absolute Stereochemistry" in: J. Am. Chem. Soc. 1996, 118. 7094-7100.

Karikomi, Michinori &al: "Regio- and stereocontrolled synthesis of novel 3-sulfonamido-2,3,4,5-tetrahydro-1,5-benzothiazepines from 2-(bromomethy)- or 2-(sulfonyloxymethyl)azitidines" in: Org. Biomiol. Chem., 2008, 6, 1902-1904.

Thorsteinsson, Thorsteinn &al; "Cycloserine Fatty Acid Derivatives as Prodrugs: Synthesis, Degradation and in Vitro Skin Permeability" in: Chem. Pharmn. Bull: 50(4) 554-557 (2002).

(56) References Cited

OTHER PUBLICATIONS

Vigorita M G et al: “Fluorocontaining D-Cycloserines, Synthesis and In Vitro Evaluation of Antimicrobial and Antiviral Activities”, IL Farmaco, vol. 47, No. 6, Jun. 1, 1992. pp. 907-918, XP000991415.
Kim, Myoung Goo et al. Journal of Antibiotics (2003), 56(2). 160-168.
Tamura et al., Synthesis of Lactivicin Analogues, Tetrahedron, vol. 44, No. 1, 1988. pp. 3231-3240.
Stammer et al. Journal of Medicinal Chemistry (1970); 13(5):1013-1015

The Cost of New Agrochemical Product Discovery, Development, and Registration in 1995, 2000, 2005-8 and 2010-2014. R&D expenditure in 2014 and expectations for 2019 4 (2016)

AGROCHEMICAL COMPOUNDS

RELATED APPLICATION INFORMATION

This application is a continuation-in-part of U.S. patent application Ser. No. 17/000,978, filed Aug. 24, 2020 (now U.S. Pat. No. 11,357,231 issued Jun. 14, 2022), which is a divisional of Ser. No. 16/267,562, filed Feb. 5, 2019 (now U.S. Pat. No. 10,750,745 issued Aug. 25, 2020), which is a divisional of U.S. application Ser. No. 15/429,631, filed Feb. 10, 2017 (now U.S. Pat. No. 10,206,400 issued Feb. 19, 2019), which is a continuation application of U.S. patent application Ser. No. 14/258,079, filed Apr. 22, 2014 (now U.S. Pat. No. 9,609,869 issued Apr. 4, 2017), which is a continuation application of U.S. patent application Ser. No. 13/512,820 filed May 30, 2012 (now U.S. Pat. No. 8,735,362 issued May 27, 2014), which is a 371 of International Application No. PCT/EP2010/068605 filed Dec. 1, 2010, which claims priority to EP 09177640.1 filed Dec. 1, 2009, and EP 10186537.6 filed Oct. 5, 2010, the contents of which are all incorporated herein by reference.

TECHNICAL FIELD

The present invention relates to isoxazolines, to processes and intermediates for preparing them, and their use as agrochemicals.

SUMMARY

Embodiments include a compound of Formula (I),

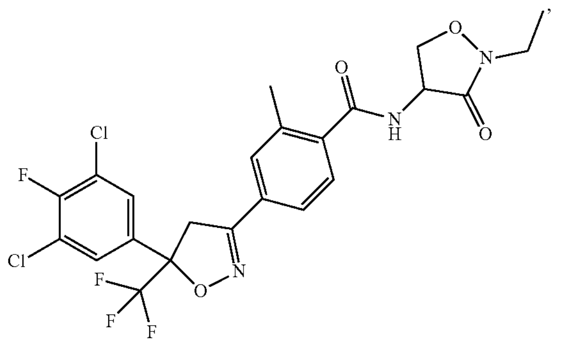 [SMILES: CCN1OCC(NC(=O)c2ccc(C3=NOC(c4cc(Cl)c(F)c(Cl)c4)(C(F)(F)F)C3)cc2C)C1=O]

or a salt or N-oxide thereof; an agrochemical composition comprising the compound of Formula (I), and one or more diluents, carriers, or auxiliaries; and a method of controlling agricultural stinkbugs, mites, thrips, caterpillars, flies, or beetles, comprising applying a pesticidally effective amount of the compound of Formula (I) to the stinkbugs, mites, thrips, caterpillars, flies, or beetles; a crop, to a locus of the stinkbugs, mites, thrips, caterpillars, flies, or beetles, or to a plant susceptible to attack by the stinkbugs, mites, thrips, caterpillars, flies, or beetles.

DETAILED DESCRIPTION

In the U.S., while there are ~330 million people, there are even more worldwide: ~7.5 billion people. Feeding the U.S., let alone the rest of the world is a difficult task. Despite the current difficulty, by 2050, the global population is expected to grow to 9.7 billion people. In response to this population growth, experts believe a 60% increase in food production is needed compared with 2005-2007 levels. *Nat Sustain* 3, 821-835 (2020). Meeting this demand will not be easy given that resources involved—such as farmable land—are finite.

In fact, while the U.S. enjoys an abundance of food, many in the world are unable to obtain their minimum nutritional needs. Therefore, food production and food security are important, pressing issues. There is general agreement, however, that the reasons we have not yet reached a full crisis is due to continuous innovation in food production and distribution. One of the most important, if not the most important innovation, has been agrochemicals.

Beyond normal nutritional needs, maximizing and maintaining food production during times of war and is of importance, and may rise to the level of national security as well as a humanitarian necessity. Accordingly, maintaining food stores and production is of importance.

As used herein, the term agrochemical includes compounds or ingredients registered or recognized as being biologically active against an agricultural pest. In general, agrochemical active ingredients include compounds listed in The Pesticide Manual, 12th edition, 2001, British Crop Protection Council. Agrochemicals include, but are not limited to herbicides, fungicides, other insecticides, bactericides, insect growth regulators, plant growth regulators, nematicides, molluscicides or mixtures of several of these preparations.

With respect to the importance of insecticides as agrochemicals, insecticides can be used to, e.g., (1) increase crop yields; (2) prevent spoilage of stored food; or (3) prevent diseases spread by pests. Moreover, insecticides can have importance in managing invasive species and protecting natural environments. Yet, discovering new insecticides is not an easy task, and there is an ever growing need due to the development of insecticide resistance in pest species.

Figure 1:
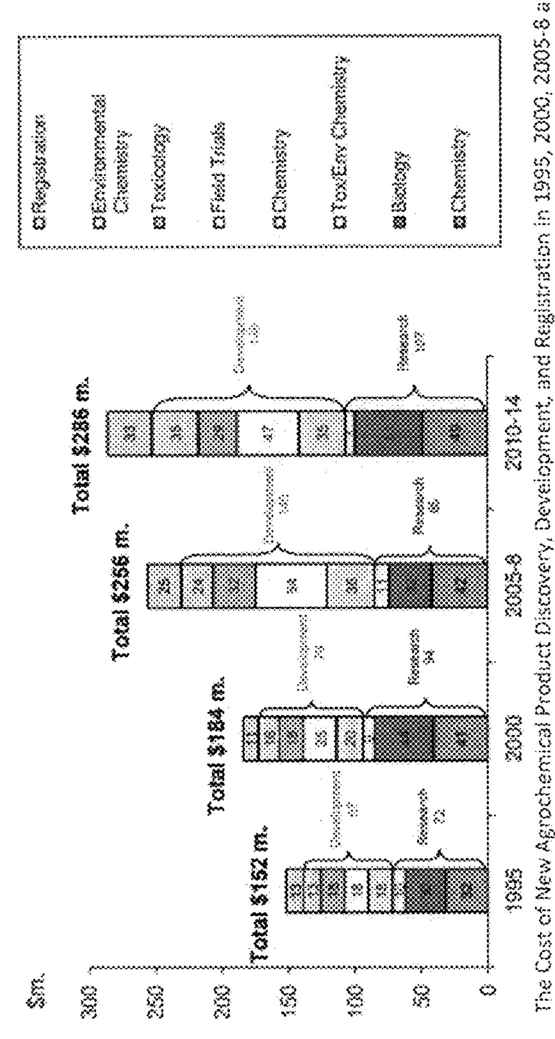
FIG. 1 provides a graphical representation of the costs of bringing a new crop protection product to market.

For instance, in 2003, it was estimated that the average cost for developing a new pesticide was more than $180 million and took 8-10 years. Charles Clift, *Intellectual Property Management in Health and Agricultural Innovation A Handbook of Best Practices* Volume Two 431, 431-435 (2007); see also Philips McDougall, *The Cost of New Agrochemical Product Discovery, Development, and Registration in* 1995, 2000, 2005-8 *and* 2010-2014. *R&D expenditure in* 2014 *and expectations for* 2019 4 (2016). During this development period, scientists would typically review 140,000 compounds. Since then, costs and development time have steadily increased. As indicated by the discovery and development costs in FIG. 1, a survey of leading crop protection companies (BASF, Bayer, Dow, DuPont, and Syngenta) found that the cost of product development has risen to $286 million. Similarly, the time from first synthesis of a new crop protection molecule to its subsequent commercial introduction has risen from 8.3 years to 11.3 years.

In general, the agrochemical development process can be split into three stages: (1) research/discovery; (2) development; and (3) registration. Research includes synthesizing hundreds of thousands of new molecules and screening them for biological activity and useful properties. The ultimate goal of research is discovering product candidates having good biological, chemical, toxicological, environmental and commercial characteristics for further development. Development encompasses the steps required to commercialize a product. This entails detailed biological and safety testing; manufacturing studies; and pilot plant startups. Once development is complete, the information produced will be sent to a regulatory body for the registration step. If the proposed product meets the registration agency's criteria, marketing of the product may begin.

The present disclosure relates to the discovery of one such compound, a compound of Formula (I), Formula (I)

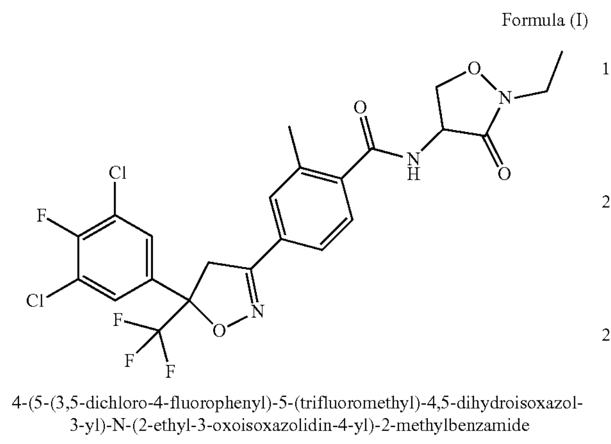

Figure 2:
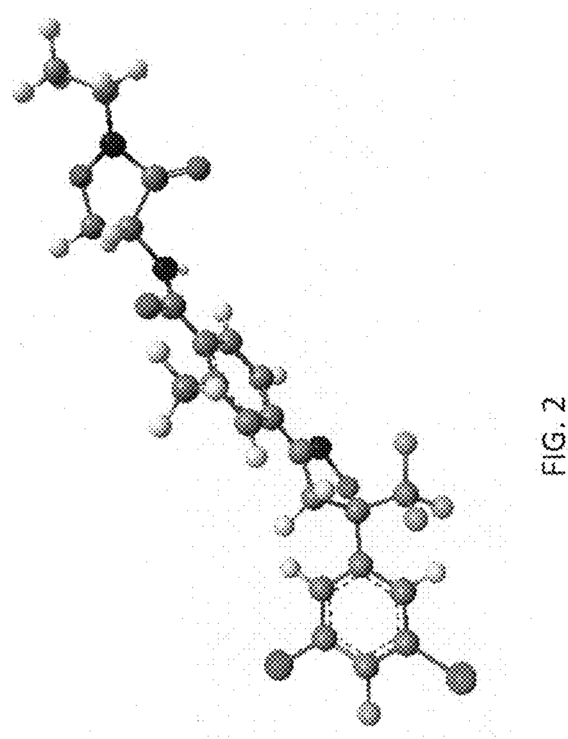
FIG. 2 provides a ball-and-stick representation of 4-((S)-5-(3,5-dichloro-4-fluorophenyl)-5-(trifluoromethyl)-4,5-dihydroisoxazol-3-yl)-N—((R)-2-ethyl-3-oxoisoxazolidin-4-yl)-2-methylbenzamide.

4-(5-(3,5-dichloro-4-fluorophenyl)-5-(trifluoromethyl)-4,5-dihydroisoxazol-3-yl)-N-(2-ethyl-3-oxoisoxazolidin-4-yl)-2-methylbenzamide and its agrochemical properties. A stick-and-ball depiction is provided in FIG. 2.

The compound of Formula (I), which has the common name "isocycloseram" and is the active ingredient in PLINAZOLIN® technology, has an identified mode of action as a GABA-gated chloride channel allosteric modulator and acts as a non-competitive GABA-gated chloride channel antagonist. This mode of action is recognized in the Insecticide Resistance Classification (IRAC) as group 30—a novel group. IRAC is a long-standing tool used for managing insecticide resistance by rotating between different modes of actions or chemical classes. Thomas C. Sparks, Ralf Nauen, *IRAC: Mode of action classification and insecticide resistance management*, Pesticide Biochemistry and Physiology, Volume 121, 2015, Pages 122-128. Accordingly, the discovery of the compound of Formula (I) was of significant importance.

PLINAZOLIN® has already been receiving praise from University researchers: "We call it the vacation spray because of its extended residual," said Sebe Brown, University of Tennessee Extension entomologist. "Theoretically, a grower could apply this technology, take a week off for summer vacation, and not be behind on insecticide sprays upon his return."

Brown delivered his remarks during the 2022 Cotton Focus meeting, hosted by the UT Institute of Agriculture.

. . .

"It is going to be a game changer in the row crop insecticide game," Brown said. "It gives us a desperately needed boost in what has become a very shallow toolbox. We need things we can rotate with—especially in cotton."

"Rotating chemistries will always be beneficial to growers," he added.

Brown had evaluated Plinazolin technology over the past four years in his former role as Field Crop and Extension Entomologist for LSU AgCenter. He joined the UT Institute of Agriculture in December. UTIA evaluations have also shown that Plinazolin exhibits extended residual activity on insect pests significant to cotton and soybean growers.

Ginger Rowsey, *Plinazolin insecticide features new mode of action, residual activity*, Delta FarmPress, Mar. 1, 2022.

The invention provides methods of combating and/or controlling pests, e.g. an invertebrate animal pest, which comprises applying to the pest, to a locus of the pest, or to a plant susceptible to attack by the pest a pesticidally effective amount of the compound of Formula (I). In particular, methods include combating and/or controlling insects, acarines, nematodes or molluscs which comprises applying an insecticidally, acaricidally, nematicidally or molluscicidally effective amount of the compound of Formula (I), or a composition containing the compound of Formula (I), to a pest, a locus of pest, preferably a plant, or to a plant susceptible to attack by a pest. The compound of Formula (I) is preferably used against insects, acarines or nematodes.

The term "plant" as used herein includes seedlings, bushes and trees.

In order to apply the compound of Formula (I) as an insecticide, acaricide, nematicide or molluscicide to a pest, a locus of pest, or to a plant susceptible to attack by a pest, the compound of Formula (I) is usually formulated into a composition which includes, in addition to the compound of Formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of the compound of formula (I). The composition is generally used for the control of pests such that a compound of Formula (I) is applied at a rate of from 0.1 g to 10 kg per hectare, preferably from 1 g to 6 kg per hectare, more preferably from 1 g to 1 kg per hectare.

When used in a seed dressing, the compound of Formula (I) is used at a rate of 0.0001 g to 10 g (for example 0.001 g or 0.05 g), preferably 0.005 g to 10 g, more preferably 0.005 g to 4 g, per kilogram of seed.

In another aspect of the disclosure a composition comprising a pesticidally effective amount of the compound of Formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged.

The compound of Formula (I) can be applied by any known means of applying pesticidal compounds. For example, the compound of Formula (I) can be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

The compound of Formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs. EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of the compound of Formula (I) (for example 0.0001 to 10%, by weight) depending upon the purpose for which they are to be used.

The compound of Formula (I) may be used in mixtures with fertilizers (for example nitrogen-, potassium- or phosphorus-containing fertilizers). Suitable formulation types include granules of fertilizer. The mixtures preferably contain up to 25% by weight of the compound of Formula (I).

The compositions can further contain other compounds having biological activity, for example micronutrients or compounds having fungicidal activity, plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Preferred crops or plants for applying the compound of Formula (I) include soybeans, corn, rice, coffee, and a wide range of fruits and vegetables—in addition to cotton. Specific crops or plants include: soy, potato, tomato, and peppers.

Preferred pests for applying the compound of Formula (I) include stinkbugs, mites, thrips, caterpillars, flies, and beetles. Specific pests include: *Tetranychus urticae; Caliothrips phaseoli; Rhyssomatus subtilis; Nezara viridula; Piezodorus guildinii; Edessa meditabunda; Dichelops furcatus; Liriomyza huidobrensis; Frankliniella occidentalis; Trips tabac; Tuta absoluta; Aculops lycopersic; Tetranichus urticae; Frankliniella occidentalis*; and *Polyphagotarsonemus latus.*

The disclosure further relates to the compound of Formula (I)'s isomers:

Formula (Ia)

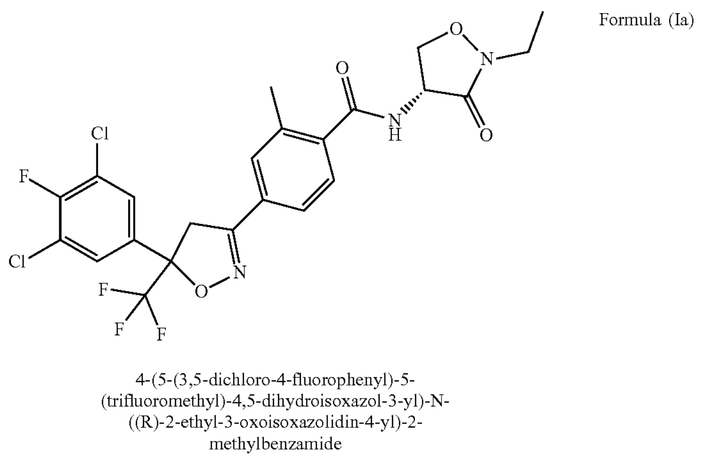

4-(5-(3,5-dichloro-4-fluorophenyl)-5-(trifluoromethyl)-4,5-dihydroisoxazol-3-yl)-N-((R)-2-ethyl-3-oxoisoxazolidin-4-yl)-2-methylbenzamide -continued Formula (Ib)

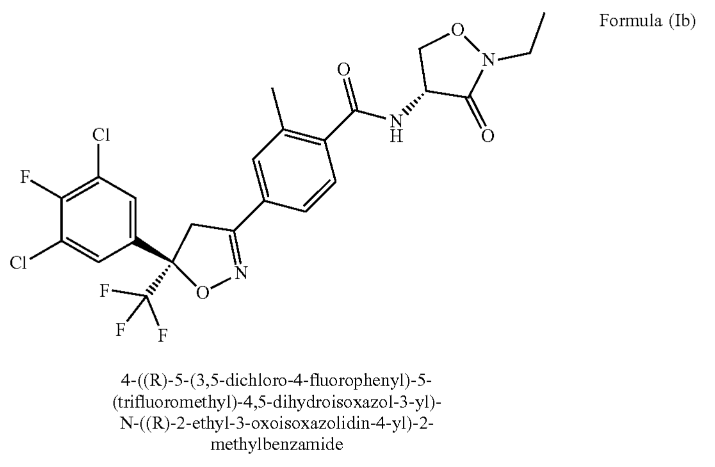

4-((R)-5-(3,5-dichloro-4-fluorophenyl)-5-(trifluoromethyl)-4,5-dihydroisoxazol-3-yl)-N-((R)-2-ethyl-3-oxoisoxazolidin-4-yl)-2-methylbenzamide Formula (Ic)

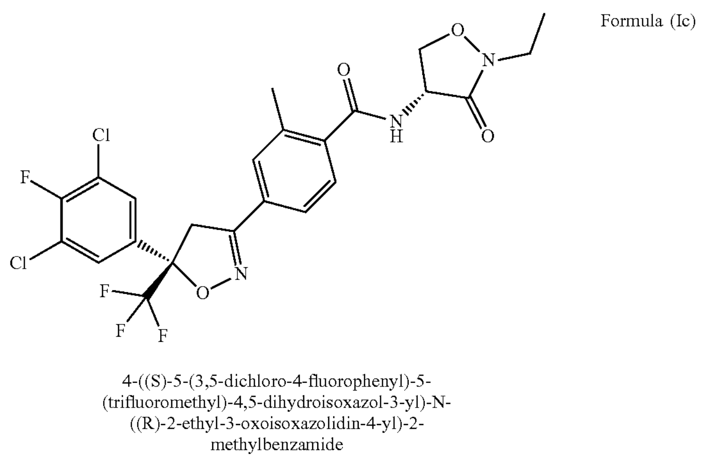

4-((S)-5-(3,5-dichloro-4-fluorophenyl)-5-(trifluoromethyl)-4,5-dihydroisoxazol-3-yl)-N-((R)-2-ethyl-3-oxoisoxazolidin-4-yl)-2-methylbenzamide Formula (Id)

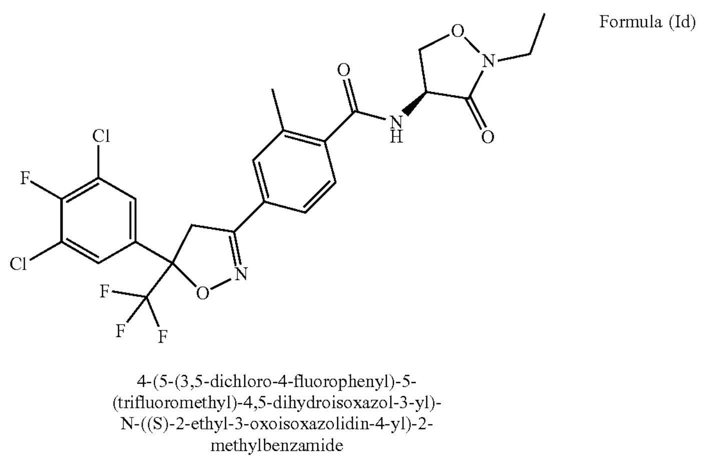

4-(5-(3,5-dichloro-4-fluorophenyl)-5-(trifluoromethyl)-4,5-dihydroisoxazol-3-yl)-N-((S)-2-ethyl-3-oxoisoxazolidin-4-yl)-2-methylbenzamide -continued Formula (Ie)

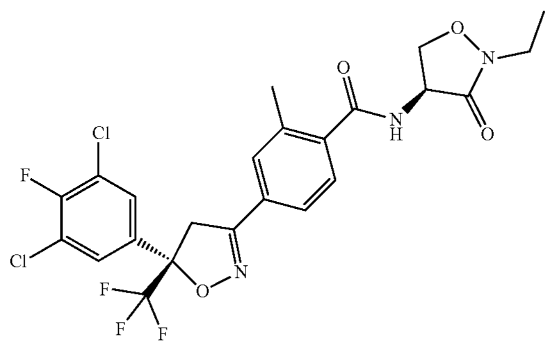 [SMILES: CCN1OC[C@H](NC(=O)c2ccc(C3=NO[C@@](c4cc(Cl)c(F)c(Cl)c4)(C(F)(F)F)C3)cc2C)C1=O]

4-((S)-5-(3,5-dichloro-4-fluorophenyl)-5-(trifluoromethyl)-4,5-dihydroisoxazol-3-yl)-N-((S)-2-ethyl-3-oxoisoxazolidin-4-yl)-2-methylbenzamide Formula (If)

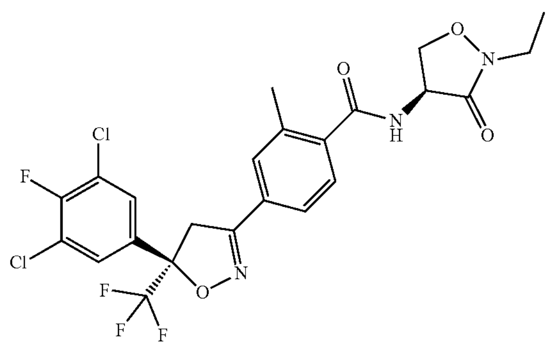 [SMILES: CCN1OC[C@H](NC(=O)c2ccc(C3=NO[C@](c4cc(Cl)c(F)c(Cl)c4)(C(F)(F)F)C3)cc2C)C1=O]

4-((R)-5-(3,5-dichloro-4-fluorophenyl)-5-(trifluoromethyl)-4,5-dihydroisoxazol-3-yl)-N-((S)-2-ethyl-3-oxoisoxazolidin-4-yl)-2-methylbenzamide Formula (Ig)

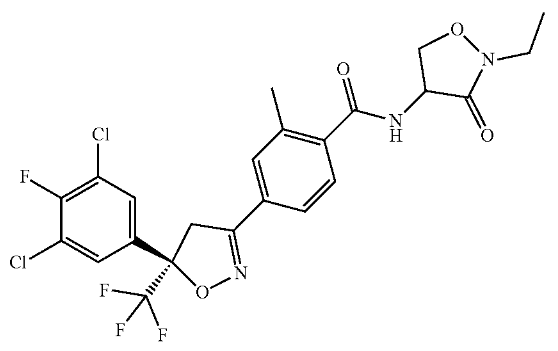 [SMILES: CCN1OCC(NC(=O)c2ccc(C3=NO[C@](c4cc(Cl)c(F)c(Cl)c4)(C(F)(F)F)C3)cc2C)C1=O]

4-((R)-5-(3,5-dichloro-4-fluorophenyl)-5-(trifluoromethyl)-4,5-dihydroisoxazol-3-yl)-N-(2-ethyl-3-oxoisoxazolidin-4-yl)-2-methylbenzamide -continued Formula (Ih)

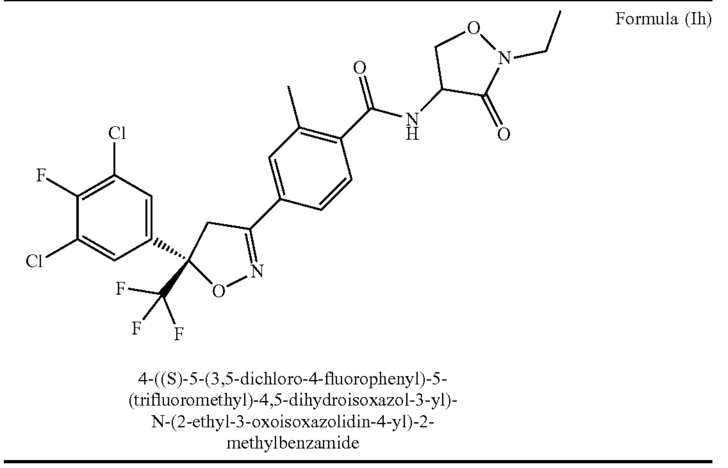

4-((S)-5-(3,5-dichloro-4-fluorophenyl)-5-(trifluoromethyl)-4,5-dihydroisoxazol-3-yl)-N-(2-ethyl-3-oxoisoxazolidin-4-yl)-2-methylbenzamide Accordingly, as indicated above, the compound of Formula I includes at least one chiral center and may exist as, e.g., compounds of Formula (Ig) or compounds of Formula (Ih).

Generally, compounds of formula (Ih) are more biologically active than compounds of formula (Ig). The disclosure includes mixtures of compounds (Ig) and (Ih) in any ratio, e.g., in a molar ratio of about 1:99 to 99:1, about 10:1 to 1:10, or a substantially 50:50 molar ratio. In an enantiomerically enriched mixture of formula (Ih), the molar proportion of compound (Ih) compared to the total amount of both enantiomers is for example greater than 50%, e.g., at least 55, 60, 65, 70, 75, 80, 85, 90, 95, 96, 97, 98, or at least 99%. Likewise, in enantiomerically enriched mixture of formula (Ig), the molar proportion of the compound of formula (Ig) compared to the total amount of both enantiomers is for example greater than 50%, e.g. at least 55, 60, 65, 70, 75, 80, 85, 90, 95, 96, 97, 98, or at least 99%. Enantiomerically enriched mixtures of formula (Ih) are preferred.

As used herein, the term "about" when referring to a measurable value such as an amount, a temporal duration, and the like, is meant to encompass variations. Such variations, however, are dependent on the specific component referred to and the context as understood by a person of ordinary skill in the art.

The compound of Formula (I) can be synthesized from methodology previously disclosed, e.g., the methodology disclosed in related U.S. Pat. No. 8,735,362 issued May 27, 2014, which is incorporated by reference in its entirety.

One skilled in the art recognizes that because in the environment, under physiological conditions, salts of chemical compounds are in equilibrium with their corresponding non-salt forms, salts share the biological utility of the non-salt forms. Thus a wide variety of salts of the compound of Formula (I) (and active ingredients used in combination with the active ingredients of the invention) may be useful. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compound of Formula (I) also includes N-oxides. Accordingly, the disclosure comprises combinations of compounds of Formula (I) including N-oxides and salts.

The compound C3 was tested for pesticidal/insecticidal properties as follows:

*Spodoptera littoralis* (Egyptian cotton leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT). The compound of Formula (I) gave at least 80% control of *Spodoptera littoralis*.

*Heliothis virescens* (Tobacco budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation. The compound C3 gave at least 80% control of *Heliothis virescens*.

*Plutella xylostella* (Diamond back moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation. The compound C3 gave at least 80% control of *Plutella xylostella*.

*Diabrotica balteata* (Corn root worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation. The compound C3 gave at least 80% control of *Diabrotica balteata*.

*Myzus persicae* (Green peach aphid), systemic test:

Roots of pea seedlings, infested with an aphid population of mixed ages, are placed directly in the test solutions at an application rate of 12.5 ppm. 6 days after introduction, samples are checked for mortality and special effects on the plant. The compound C3 gave at least 80% control of *Myzus persicae*.

*Thrips tabaci* (Onion thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality. The compound C3 gave at least 80% control of *Thrips tabaci*.

*Tetranychus urticae* (Two-spotted spider mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality. The compound C3 gave at least 80% control of *Tetranychus urticae*.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

The invention claimed is:

1. A compound of Formula (I),

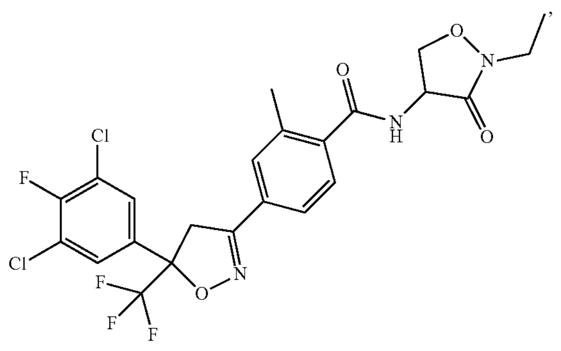 [SMILES: CCN1OCC(NC(=O)c2ccc(C3=NOC(c4cc(Cl)c(F)c(Cl)c4)(C(F)(F)F)C3)cc2C)C1=O]

or a salt or N-oxide thereof.

2. The compound of claim 1, wherein the compound is not a salt or N-oxide thereof.

3. The compound of either claim 1 or 2, wherein the compound is the compound of Formula (Ia),

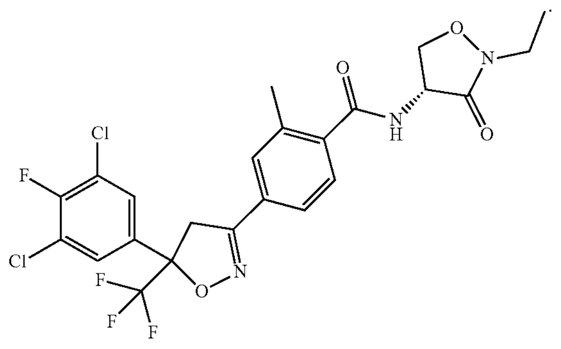 [SMILES: CCN1OC[C@@H](NC(=O)c2ccc(C3=NOC(c4cc(Cl)c(F)c(Cl)c4)(C(F)(F)F)C3)cc2C)C1=O]

4. The compound of either claim 1 or 2, wherein the compound is the compound of Formula (Ib),

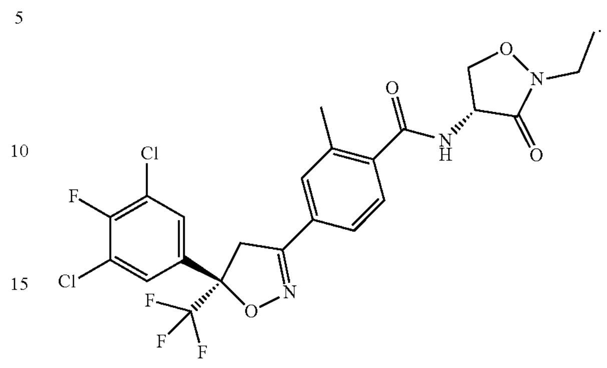

5. The compound of either claim 1 or 2, wherein the compound is the compound of Formula (Ic),

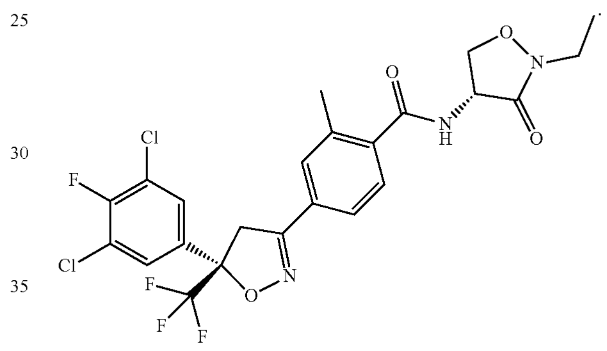

6. The compound of either claim 1 or 2, wherein the compound is the compound of Formula (Id),

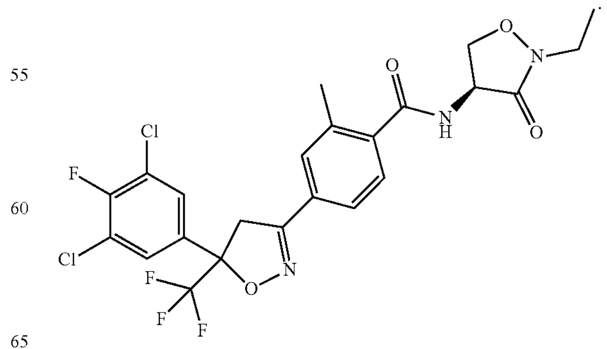

7. The compound of either claim 1 or 2, wherein the compound is the compound of Formula (Ie),

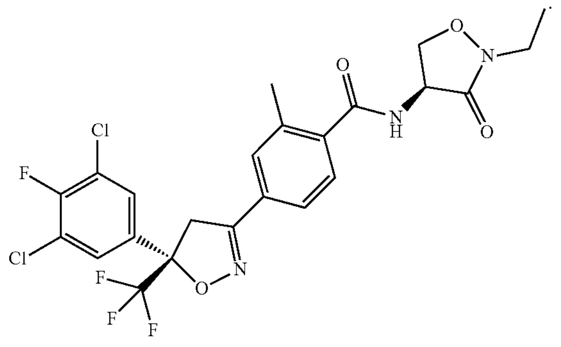 [SMILES: CCN1OC[C@H](NC(=O)c2ccc(C3=NO[C@@](c4cc(Cl)c(F)c(Cl)c4)(C(F)(F)F)C3)cc2C)C1=O]

8. The compound of either claim 1 or 2, wherein the compound is the compound of Formula (If),

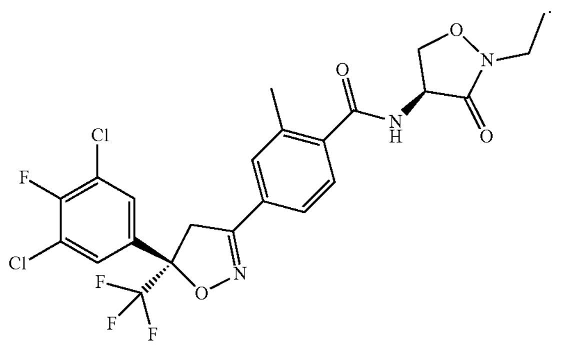 [SMILES: CCN1OC[C@H](NC(=O)c2ccc(C3=NO[C@](c4cc(Cl)c(F)c(Cl)c4)(C(F)(F)F)C3)cc2C)C1=O]

9. The compound of either claim 1 or 2, wherein the compound is the compound of Formula (Ig),

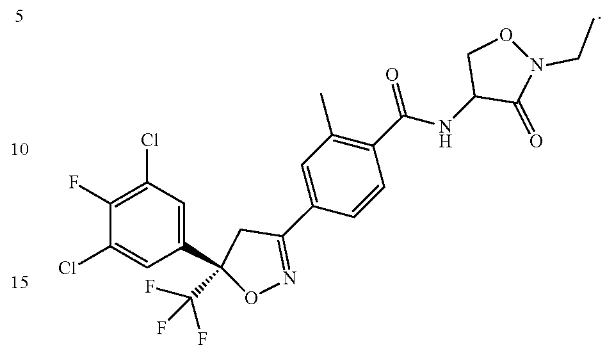

10. The compound of either claim 1 or 2, wherein the compound is the compound of Formula (Ih),

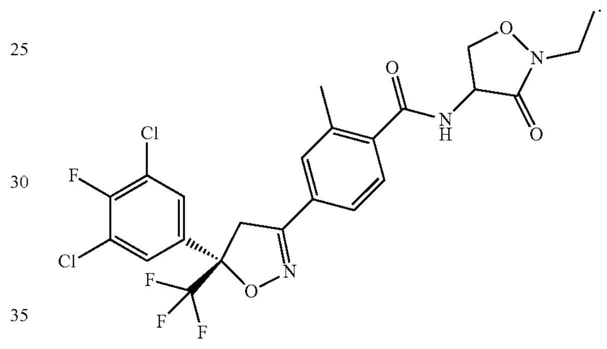

11. An agrochemical composition comprising: the compound of claim 1 and one or more diluents, carriers, or auxiliaries.

12. The agrochemical composition of claim 11, wherein the composition is a concentrated agrochemical composition.

13. A method of controlling agricultural stinkbugs, mites, *thrips*, caterpillars, flies, or beetles, comprising: applying a pesticidally effective amount of the compound of claim 1 to the stinkbugs, mites, *thrips*, caterpillars, flies, or beetles; a crop, to a locus of the stinkbugs, mites, *thrips*, caterpillars, flies, or beetles, or to a plant susceptible to attack by the stinkbugs, mites, *thrips*, caterpillars, flies, or beetles.

14. A composition comprising: 4-[(5RS)-5-(3,5-dichloro-4-fluorophenyl)-4,5-dihydro-5-(trifluoromethyl) isoxazol-3-yl]-N-[(4RS)-2-ethyl-3-oxoisoxazolidin-4-yl]-o-toluamide wherein 80-100% is the (5S,4R)-isomer.

* * * * *